United States Patent

Varma et al.

[11] 3,937,720
[45] Feb. 10, 1976

[54] STEROIDAL[16α,17-β]NAPHTHALENES

[75] Inventors: Ravi K. Varma, Belle Mead; Christopher M. Cimarusti, Hamilton, both of N.J.

[73] Assignee: E. R. Squibb & Sons, Inc., Princeton, N.J.

[22] Filed: Nov. 25, 1974

[21] Appl. No.: 526,866

[52] U.S. Cl. .......................... 260/397.45; 260/397.1
[51] Int. Cl.² .......................................... C07C 3/00
[58] Field of Search ...... Machine Searched Steroids; 260/397.45

[56] References Cited
OTHER PUBLICATIONS
Wasserman et al., Journ. of the Amer. Chem. Soc., 1965, Vol. 87, No. 17, pp. 4002–4003.

*Primary Examiner*—Elbert L. Roberts
*Attorney, Agent, or Firm*—Lawrence S. Levinson; Merle J. Smith; Donald J. Barrack

[57] ABSTRACT
Novel steroids having the structure

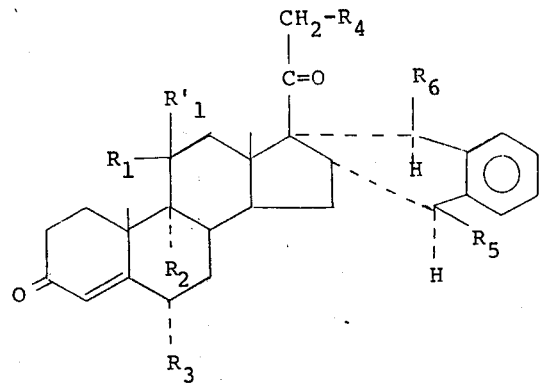

and the 1,2-dehydro derivatives thereof, wherein $R_1$ is chlorine, fluorine, or hydroxy and $R'_1$ is hydrogen or $R_1$ and $R'_1$ together are =O; $R_2$ is hydrogen or halogen; $R_3$ is hydrogen, methyl, or fluorine; $R_4$ is hydrogen, hydroxy,

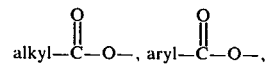

or halogen; $R_5$ and $R_6$ are the same or different and are hydrogen, alkyl, alkylthio, alkoxy, carboalkoxy, formyl,

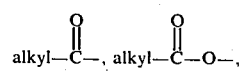

hydroxy, halogen, phenyl or cyano, with the proviso that when $R_5$ and $R_6$ are different, one of $R_5$ and $R_6$ is hydrogen.

17 Claims, No Drawings

STEROIDAL[16α,17-b]NAPHTHALENES

BRIEF DESCRIPTION OF THE INVENTION

Steroidal[16α,17-b]naphthalenes having the structure

I

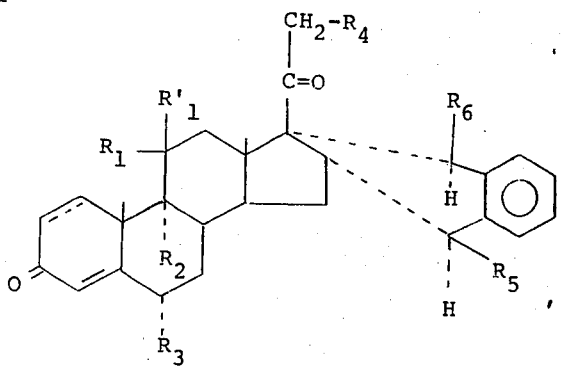

are useful topical and systemic antiinflammatory agents. In formula I, and throughout the specification, the symbols are as defined below:

$R_1$ is chlorine, fluorine or hydroxy and $R'_1$ is hydrogen or $R_1$ and $R'_1$ together are =O;

$R_2$ is hydrogen or halogen;

$R_3$ is hydrogen, methyl or fluorine;

$R_4$ is hydrogen, hydroxy,

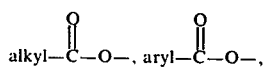

or halogen; and $R_5$ and $R_6$ are the same or different and are hydrogen, alkyl, alkylthio, alkoxy, carboalkoxy, formyl,

hydroxy, halogen, phenyl or cyano, with the proviso that when $R_5$ and $R_6$ are different, one of $R_5$ and $R_6$ is hydrogen.

The dotted line in the 1,2-position of the steroid of formula I represents the optional presence of a double bond.

The term "alkyl," as used throughout the specification, refers to straight or branched chain hydrocarbon groups having 1 to 6 carbon atoms.

The term "alkoxy," as used throughout the specification, refers to groups having the formula Y—O— wherein Y is alkyl as defined above.

The term "aryl," as used throughout the specification, refers to phenyl or phenyl substituted with alkyl, alkoxy, or halogen; phenyl is preferred.

The term "halogen," as used throughout the specification, refers to fluorine, chlorine, bromine, and iodine; fluorine, chlorine, and bromine are preferred.

DETAILED DESCRIPTION OF THE INVENTION

The steroids of formula I are physiologically active substances which possess glucocorticoid and antiinflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a dosage range of 0.1 to 200 milligrams, preferably 0.3 to 100 milligrams. If administered topically, the compounds of this invention may be used in the range of 0.01 to 5.0% by weight, preferably 0.05 to 2.0% by weight, in a conventional cream or lotion.

The steroids of formula I wherein $R_4$ is hydrogen,

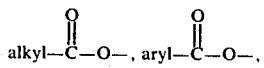

or halogen can be prepared by reacting a benzocyclobutene having the structure

II

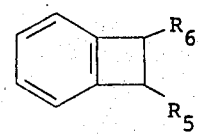

with a steroid having the structure

III

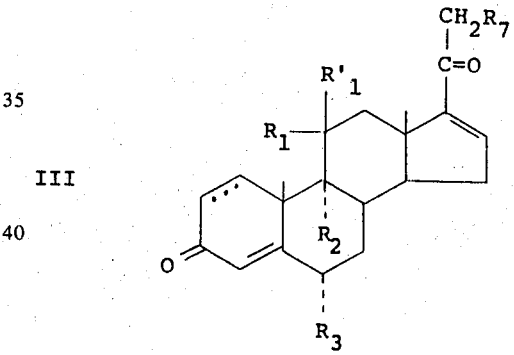

to yield a steroid having the structure

IV

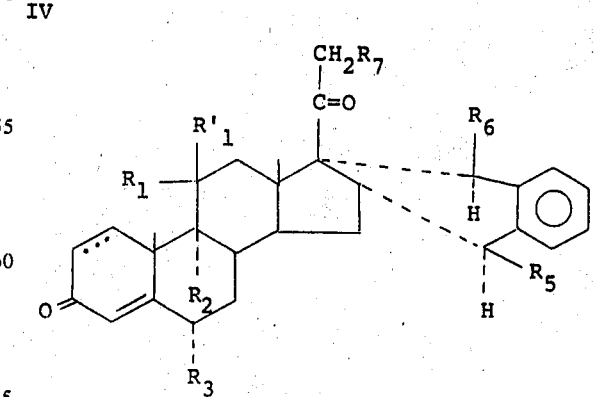

In formulas III and IV, and throughout the specification, $R_7$ can be hydrogen,

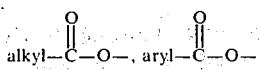

or halogen. The above reaction can be run with or without an inert solvent. Preferably, the reaction will be run neat, in an inert atmosphere, at temperatures up to the boiling point of the solution.

Those steroids of formula I wherein $R_4$ is hydroxy or halogen can be prepared from the corresponding 21-acyloxy steroid of formula IV. Hydrolysis of the 21-acyloxy steroid yields the corresponding 21-hydroxy steroid which can in turn be converted to a 21-halo steroid using procedures well known in the art.

Alternatively, the compounds of formula I can be prepared from benzocyclobutenes of formula II and steroids having the structure

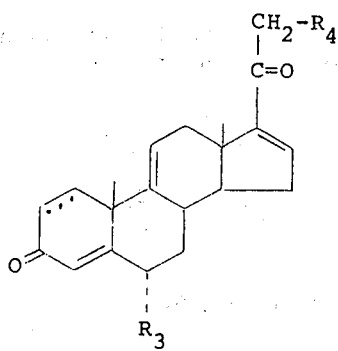

V

Reaction of a benzocyclobutene of formula II and a steroid of formula V yields a steroid having the structure

VI

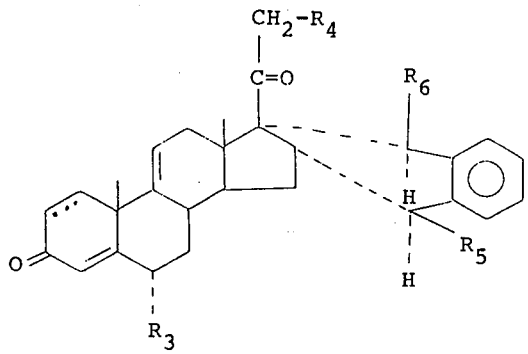

A steroid of formula VI can be converted to the corresponding 9,11$\beta$-dihalo steroid or 9-halo-11 1$\beta$-hydroxy steroid using procedures well known in the art. The 21-acyloxy steroids can be readily converted to the corresponding 21-hydroxy and 21-halo steroids.

Many variations of the above described procedures will be apparent to a person of ordinary skill in the art.

The following examples are specific embodiments of this invention.

EXAMPLE 1

9-Fluoro-1',2',3',4'-tetrahydro-11$\beta$-hydroxypregn-4-eno[16$\alpha$,17-b]naphthalene-3,20-dione 9-Fluoro-11$\beta$-hydroxypregna-4,16-diene-3,20-dione (100 mg) and benzocyclobutene (1.5 ml) are refluxed under nitrogen for 18 hours while a crystalline solid separates from solution. The unreacted benzocyclobutene is recovered by distillation in vacuo leaving a residual solid (115 mg). One crystallization of this form chloroform-hexane yields the title compound, melting point 270°–271°C, dec.

EXAMPLE 2

21-(Acetyloxy)-9-fluoro-1',2',3',4'-tetrahydro-11$\beta$-hydroxypregna-1,4-dieno[16$\alpha$,17-b]naphthalene-3,20-dione 21-(Acetyloxy)-9-fluoro-11$\beta$-hydroxypregna-1,4,16-triene-3,20-dione (500 mg) is refluxed under nitrogen for 34 hours with 5 ml of benzocyclobutene. The solution is cooled, diluted with 10 ml of 1:3 hexane-chloroform, and chromatographed on a 60 g-silica gel column. Elution with 1:3 hexane-chloroform, 1:4 hexane-chloroform and 1:9 hexane-chloroform yields 490 mg of material. Crystallization from acetone-hexane yields 400 mg of the title compound, melting point 236°–237°C.

EXAMPLE 3

21-(Acetyloxy)-9-fluoro-1',2',3',4'-tetrahydro-11$\beta$-hydroxypregn-4-eno[16$\alpha$,17-b]naphthalene-3,20-dione A mixture of 500 mg of 21-(acetyloxy)-9-fluoro-11$\beta$-hydroxypregna-4,16-diene-3,20-dione and 5 ml of benzocyclobutene is refluxed under nitrogen for 36 hours. The resulting slurry is cooled, dissolved in 1:9 hexane-chloroform and chromatographed on a 40 g-silica gel column. Elution with 1:3 hexane-chloroform and 1:4 hexane-chloroform yields 550 mg material. Two recrystallizations from acetone-hexane yield 310 mg of the title compound, melting point 261°–262°C.

EXAMPLE 4

21-(Acetyloxy)-4'$\beta$-ethoxy-9-fluoro-1',2',3',4'-tetrahydro-11$\beta$-hydroxypregna-1,4-dieno[16$\alpha$,17-b]-naphthalene-3,20-dione A suspension of 21-(acetyloxy)-9-fluoro-11$\beta$-hydroxypregna-1,4,16-triene-3,20-dione (1.0 g) in 1-ethoxy-1,2-dihydrobenzocyclobutene (3.0 g) is stirred under nitrogen in a bath at 160°C. In a few seconds, the steroid dissolves and a vigorous reaction occurs. After 10 minutes, examination of an aliquot by thin layer chromatography (tlc) reveals the absence of the starting steroid. The reaction is, however, continued for 18 hours with no significant difference in the tlc behavior. The cooled reaction mixture is then poured on a column of silica gel (100 g) made up in chloroform. Elution with chloroform and chloroform-ethyl acetate (98:2) affords a gum (2.43 g). Elution of the column with chloroform-ethyl acetate (90:10) affords five fractions which are all impure to different degrees. These are combined to afford a foam (570 mg).

The gum (2.43 g) is dissolved in ethanol-tetrahydrofuran (1:1, 30 ml) and two drops of concentrated hydrochloric acid are added. After 6.0 hours sodium acetate (0.5 g) is added and the solution is evaporated to dryness. The residue is combined with the foam (570 mg) and is chromatographed over silica gel (90 g). Elution with chloroform affords an oil which is discarded. Elution with chloroformethyl acetate (98:2) affords the title compound as a solid (800 mg). Further elution of the column with chloroformethyl acetate (95:5, 80:20) affords a mixture (430 mg) of four steroidal compounds, one of which is identical with the title compound. One crystallization of the 800 mg of solid from chloroform-ethyl acetate yields the title compound (633 mg), melting point 283°–284°C, dec.

EXAMPLE 5

21-(Acetyloxy)-9-fluoro-1',2',3',4'-tetrahydro-11β-hydroxy-3,20-dioxopregna-1,4-dieno[16α,17-b]-naphthalene-4'β-carbonitrile 21-(Acetyloxy)-9-fluoro-11β-hydroxypregna-1,4,16-triene-3,20-dione (402 mg) is dissolved in dry xylene (12 ml) by heating in a bath at 135°C under nitrogen. The solution is then cooled, 1-cyano-1,2-dihydrobenzocyclobutene (645 mg) is added, and reheated at 135°C (bath temperature). In a few hours, a solid starts to separate. After 30 hours the mixture is cooled to room temperature and the solid is separated by filtration (255 mg). This is washed with hot chloroformtetrahydrofuran (1:1) to yield the title compound (200 mg), melting point 317°–318°C, dec.

EXAMPLE 6

4'β,21-bis[Acetyloxy]-9-fluoro-1',2',3',4'-tetrahydro-11β-hydroxypregna-1,4-dieno[16α,17-b]-naphthalene-3,20-dione A solution of 21-(acetyloxy)-9-fluoro-11β-hydroxypregna-1,4,16-triene-3,20-dione (622 mg) in orthodichlorobenzene (7.0 ml) containing 1-acetoxy-1,2-dihydrobenzocyclobutene (1.13 g) is heated under nitrogen in a bath at 160°C for 20 hours. The solvent is then evaporated in vacuo and the residue is applied to two 2.0 × 200 × 200 mm silica gel plates. The plates are developed four times with chloroformethyl acetate (7:3). The two major bands due to the products are extracted with chloroform-methanol (98:2). One crystallization of the less polar material from acetone-hexane yields the title compound (213 mg), melting point 272°–273.5°C, dec.

EXAMPLE 7

9-Fluoro-1',2',3',4'-tetrahydro-11β,21-dihydroxypregna-1,4-dieno[16α,17-b]naphthalene-3,20-dione A solution of 21-(acetyloxy)-9-fluoro-1',2',3',4'-tetrahydro-11β-hydroxypregna-1,4-dieno[16α,17-b]naphthalene-3,20-dione (1.3 g, prepared as described in Example 2) in 30 ml of methanol and 20 ml of tetrahydrofuran is stirred at 0°C under nitrogen for 1.5 hours with 0.5 ml of 10% potassium carbonate. The resulting solution is neutralized with 5% acetic acid, poured into cold water and extracted with chloroform. The chloroform solution is washed with water and dried over anhydrous sodium sulfate. The solvent is then evaporated in vacuo. Two recrystallizations of the resultant material from chloroform-methanol give 500 mg of the title compound, melting point 293°–294°C.

EXAMPLE 8

21-Chloro-9-fluoro-1',2',3',4'-tetrahydro-11β-hydroxypregna-1,4-dieno[16α,17-b]naphthalene-3,20-dione A. 21-(Methanesulfonyloxy)-9-fluoro-1',2',3',4'-tetrahydro-11β-hydroxypregna-1,4-dieno[16α,17-b]naphthalene-3,20-dione A solution of 9-fluoro-1',2',3',4'-tetrahydro-11β,21-dihydroxypregna-1,4-dieno[16α,17-b]naphthalene-3,20-dione (800 mg, prepared as described in Example 7) in 45 ml of pyridine is stirred at 0°C under nitrogen for 2.5 hours with 0.5 ml of methanesulfonyl chloride. The resulting solution is poured into cold 5% hydrochloric acid and extracted with chloroform. The chloroform solution is washed with water, dried over anhydrous sodium sulfate and evaporated in vacuo to give 1.07 g of the title compound.

B. 21-Chloro-9-fluoro-1',2',3',4'-tetrahydro-11β-hydroxypregna-1,4-dieno[16α,17-b]naphthalene-3,20-dione A solution of 1.07 g of 21-(methanesulfonyloxy)19-fluoro-1',2',3',4'-tetrahydro-11β-hydroxypregna-1,4-dieno-[16α,17-b]naphthalene-3,20-dione in 100 ml of dimethylformamide is refluxed under nitrogen for 1.5 hours with 1.1 g of lithium chloride. The solution is cooled, diluted with cold water, stirred for 25 minutes and filtered. The solid is dissolved in chloroform, washed with 5% hydrochloric acid and water, dried over anhydrous magnesium sulfate and evaporated in vacuo. Three recrystallizations of the resultant material from chloroform-methanol give 340 mg of the title compound, melting point 283°–284°C.

EXAMPLES 9 – 24

Following the procedure of Example 5, but substituting the benzocyclobutene listed in column I for 1-cyano-1,2-dihydrobenzocyclobutene and the steroid listed in column II for 21-(acetyloxy)-9-fluoro-11β-hydroxypregna-1,4,16-triene-3,20-dione, the steroid listed in column III is obtained.

| Example | Column I | Column II | Column III |
| --- | --- | --- | --- |
| 9 | trans-1,2-diethoxy-benzocyclobutene | 21-(acetyloxy)-9-fluoro-11β-hydroxypregna-1,4,16-triene-3,20-dione | 21-(acetyloxy)-1'β,4'β-diethoxy-9-fluoro-1',2',3',4'-tetrahydro-11β-hydroxypregna-1,4-dieno[16α,17-b]naphthalene-3,20-dione |
| 10 | 1-carbomethoxybenzocyclobutene | 21-(acetyloxy)-9-fluoro-11β-hydroxypregna-1,4,16-triene-3,20-dione | 21-(acetyloxy)-9-fluoro-1',2'-3',4'-tetrahydro-11β-hydroxy-3,20-dioxopregna-1,4-dieno-[16α,17-b]naphthalene-4'β-oic acid, methyl ester |
| 11 | trans-1,2-dicarbomethoxybenzocyclobutene | 21-(acetyloxy)-9-fluoro-11β-hydroxypregna-1,4,16-triene-3,20-dione | 21-(acetyloxy)-9-fluoro-1',2'-3',4'-tetrahydro-11β-hydroxy-3,20-dioxopregna-1,4-dieno-[16α,17-b]naphthalene-1'β,4'β-dioic acid, dimethyl ester |
| 12 | trans-1,2-dibromobenzocyclobutene | 21-(acetyloxy)-9-fluoro-11β-hydroxypregna-1,4,16-triene-3,20-dione | 21-(acetyloxy)-1'β,4'β-dibromo-9-fluoro-1',2',3',4'-tetrahydro-11β-hydroxypregna-1,4-dieno[16α,17-b]naphthalene-3,20-dione |

-Continued

| Example | Column I | Column II | Column III |
|---|---|---|---|
| 13 | 1-acetylbenzocyclo-butene | 21-(acetyloxy)-9-fluoro-11β-hydroxypregna-1,4,16-triene-3,20-dione | 21-(acetyloxy)-4'-acetyl-9-fluoro-1',2',3',4'-tetrahydro-11β-hydroxypregna-1,4-dieno[16α,17-b]naphthalene-3,20-dione |
| 14 | 1-methylthiobenzo-cyclobutene | 21-(acetyloxy)-9-fluoro-11β-hydroxypregna-1,4,16-triene-3,20-dione | 21-(acetyloxy)-4'β-methylthio-9-fluoro-1',2',3',4'-tetrahydro-11β-hydroxypregna-1,4-dieno-[16α,17-b]naphthalene-3,20-dione |
| 15 | 1-bromobenzocyclo-butene | 21-(acetyloxy)-9-fluoro-11β-hydroxypregna-1,4,16-triene-3,20-dione | 21-(acetyloxy)-4'β-bromo-9-fluoro-1',2',3',4'-tetrahydro-11β-hydroxypregna-1,4-dieno[16α,17-b]-naphthalene-3,20-dione |
| 16 | 1-ethylthiobenzo-cyclobutene | 21-(acetyloxy)-6α-fluoro-pregna-1,4,16-triene-3,11,20-trione | 21-(acetyloxy)-4'β-ethylthio-6α-fluoro-1',2',3',4'-tetrahydro-pregna-1,4-dieno[16α,17-b]-naphthalene-3,11,20-trione |
| 17 | 1-acetyloxybenzo-cyclobutene | 21-(acetyloxy)-6α-fluoro-pregna-1,4,16-triene-3,11,20-trione | 4'β,21-bis-(acetyloxy)-6α-fluoro-1',2',3',4'-tetrahydropregna-1,4-dieno[16α,17-b]naphthalene-3,11,20-trione |
| 18 | 1-formylbenzocyclo-butene | 21-(acetyloxy)-6α-methyl-pregna-1,4,16-triene-3,11,20-trione | 21-(acetyloxy)-4'β-formyl-1',2',3',4'-tetrahydro-6α-methylpregna-1,4-dieno[16α,17-b]naphthalene-3,11,20-trione |
| 19 | 1-acetyloxybenzo-cyclobutene | 21-(acetyloxy)-6α,9-di-fluoro-11β-hydroxypregna-1,4,16-triene-3,20-dione | 4'β,21-bis(acetyloxy)-6α,9-di-fluoro-1',2',3',4'-tetrahydro-11β-hydroxypregna-1,4-dieno-[16α,17-b]naphthalene-3,20-dione |
| 20 | 1-carbomethoxybenzo-cyclobutene | 21-(acetyloxy)-6α,9-di-fluoro-11β-hydroxypregna-1,4,16-triene-3,20-dione | 21-(acetyloxy)-6α,9-difluoro-1',2',3',4'-tetrahydro-11β-hydroxy-3,20-dioxopregna-1,4-dieno[16α,17-b]naphthalen-4'β-oic acid, methyl ester |
| 21 | benzocyclobutene | 21-(acetyloxy)-6α,9-di-fluoro-11β-hydroxypregna-1,4,16-triene-3,20-dione | 21-(acetyloxy)-6α,9-difluoro-1',2',3',4'-tetrahydro-11β-hydroxypregna-1,4-dieno[16α,17-b] -naphthalene-3,20-dione |
| 22 | benzocyclobutene | 21-(acetyloxy)-11β-hydroxypregna-1,4,16-triene-3,20-dione | 21-(acetyloxy)-1',2',3',4'-tetrahydro-11β-hydroxypregna-1,4-dieno-[16α,17-b]naphthalene-3,20-dione |
| 23 | 1-ethoxybenzocyclo-butene | 21-chloro-11β-hydroxypregna-4,16-dieno-3,20-dione | 21-chloro-1',2',3',4'-tetrahydro-11β-hydroxypregn-4-eno[16α,17-b]-naphthalene-3,20-dione |
| 24 | benzocyclobutene | 21-(benzoyloxy)-11β-hydroxypregna-1,4,16-triene-3,20-dione | 21-(benzoyloxy)-1',2',3',4'-tetrahydro-11β-hydroxypregna-1,4-dieno-[16α,17-b]naphthalene-3,20-dione |

EXAMPLE 25

21-(Acetyloxy)-9chloro-4'β-ethyl-6α,11β-difluoro-1',2',3',4'-tetrahydropregna-1,4-dieno[16α,17-b]naphthalene-3,20-dione A. 21-(Acetyloxy)-4'β-ethyl-6α-fluoro-1',2',3',4'-tetrahydropregna-1,4,9(11)-trieno[16α,17-b]naphthalene-3,20-dione 21-(Acetyloxy)-6α-fluoropregna-1,4,9(11), 16-tetraene-3,20-dione (2 mmoles) is dissolved in dry xylene (10 ml) by heating in a bath at 135°C under nitrogen. The solution is cooled, 1-ethyl-1,2-dihydrobenzocyclobutene (4 mmoles) is added, and the reaction mixture is heated at 135°C (bath temperature) to yield the title compound.

B. 21-(Acetyloxy)-9-chloro-4'β-ethyl-6α,11β-difluoro-1',2',3',4'-tetrahydropregna-1,4-dieno[16α,17-b]naphthalene-3,20-dione A mixture of 21-(acetyloxy)-4'β-ethyl-6α-fluoro-1',2',3',4'-tetrahydropregna-1,4,9(11)-trieno[16α,17-b]naphthalene-3,20-dione (1.5 mmoles) and N-chlorosuccinimide (1.5 mmoles) in dichloromethane is added to a mixture of anhydrous hydrogen fluoride (10 g) and anhydrous tetrahydrofuran (18 g) in a polyethylene bottle at −80°C. After 1 hour, the mixture is stirred an additional 2 hours at 0°C and poured cautiously into cold sodium carbonate solution. Extraction with chloroform gives the title compound.

EXAMPLE 26

21-(Acetyloxy)-9,11β-dichloro-1',2',3',4'-tetrahydro-4'β-phenylpregna-1,4-dieno[16α,17-b]naphthalene-3,20-dione A. 21-(Acetyloxy)-1',2',3',4'-tetrahydro-4'β-phenylpregna-1,4,9(11)-trieno[16α,17-b]naphthalene-3,20-dione 21-(Acetyloxy)pregna-1,4,9(11),16-tetraene-3,20-dione (2 mmoles) is dissolved in dry xylene (10ml) by heating in a bath at 135°C under nitrogen. The solution is cooled, 1-phenyl-1,2-dihydrobenzocyclobutene (4 mmoles) is added, and the reaction mixture is heated at 135°C (bath temperature) to yield the title compound.

B. 21-(Acetyloxy)-9,11β-dichloro-1',2',3',4'-tetrahydro-4'β-phenylpregna-1,4-dieno[16α,17-b]naphthalene-3,20-dione A solution of 21-(acetyloxy)-1',2',3',4'-tetrahydro-4'β-phenylpregna-1,4,9(11)-trieno[16α,17-b]naphthalene-3,20-dione (1.5 mmoles) and lithium chloride (2.5 g) in 25 ml of glacial acetic acid is stirred at 0°–5°C and 207 mg of N-chlorosuccinimide is added. A solution of 63 mg of dry hydrogen chloride in 1 ml of tetrahydrofuran is added and the resulting mixture is stirred at room temperature for 2 hours, poured into 300 ml of cold water, and extracted with chloroform. The chloroform solution is washed with water, dried and evaporated in vacuo to yield the title compound.

What is claimed is:
1. A steroid having the structure

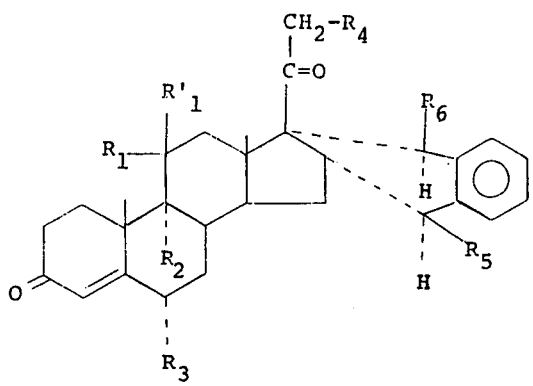

and the 1,2-dehydro derivative thereof, wherein $R_1$ is chlorine, fluorine or hydroxy and $R'_1$ is hydrogen or $R_1$ and $R'_1$ together are =O; $R_2$ is hydrogen or halogen; $R_3$ is hydrogen, methyl or fluorine; $R_4$ is hydrogen, hydroxy,

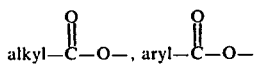

or halogen; and $R_5$ and $R_6$ are the same or different and are hydrogen, alkyl, alkylthio, alkoxy, carboalkoxy, formyl,

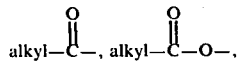

hydroxy, halogen, phenyl or cyano, with the proviso that when $R_5$ and $R_6$ are different, one of $R_5$ and $R_6$ is hydrogen.

2. A steroid in accordance with claim 1 wherein $R_2$ is fluorine.

3. A steroid in accordance with claim 1 wherein $R_3$ is hydrogen.

4. A steroid in accordance with claim 1 wherein $R_4$ is hydrogen.

5. A steroid in accordance with claim 1 wherein $R_4$ is hydroxy.

6. A steroid in accordance with claim 1 wherein $R_4$ is

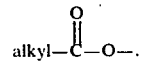

7. A steroid in accordance with claim 1 wherein $R_4$ is halogen.

8. A steroid in accordance with claim 1 wherein $R_4$ is chlorine.

9. A steroid in accordance with claim 1 wherein $R_5$ and $R_6$ are hydrogen.

10. The steroid in accordance with claim 1 having the name 9-fluoro-1',2',3',4'-tetrahydro-11β-hydroxypregn-4-eno[16α,17-b]naphthalene-3,20-dione.

11. The steroid in accordance with claim 1 having the name 21-(acetyloxy)-9-fluoro-1',2',3',4'-tetrahydro-11β-hydroxypregna-1,4-dieno[16α,17-b]naphthalene-3,20-dione.

12. The steroid in accordance with claim 1 having the name 21-(acetyloxy)-9-fluoro-1',2',3',4'-tetrahydro-11β-hydroxypregn-4-eno[16α,17-b]naphthalene-3,20-dione.

13. The steroid in accordance with claim 1 having the name 21-(acetyloxy)-4'β-ethoxy-9-fluoro-1',2',3',4'-tetrahydro-11β-hydroxypregna-1,4-dieno[16α,17-b]naphthalene-3,20-dione.

14. The steroid in accordance with claim 1 having the name 21-(acetyloxy)-9-fluoro-1',2',3',4'-tetrahydro-11β-hydroxypregna-1,4-dieno[16α,17-b]naphthalene-3,20-dione-4'β-carbonitrile.

15. The steroid in accordance with claim 1 having the name 4'β,21-bis(acetyloxy)-9-fluoro-1',2',3',4'-tetrahydro-11β-hydroxypregna-1,4-dieno[16α,17-b]naphthalene-3,20-dione.

16. The steroid in accordance with claim 1 having the name 9-fluoro-1',2',3',4'-tetrahydro-11β,21-dihydroxypregna-1,4-dieno[16α,17-b]naphthalene-3,20-dione.

17. The steroid in accordance with claim 1 having the name 21-chloro-9-fluoro-1',2',3',4'-tetrahydro-11β-hydroxypregna-1,4-dieno[16α,17-b]naphthalene-3,20-dione.

* * * * *

UNITED STATES PATENT AND TRADEMARK OFFICE
CERTIFICATE OF CORRECTION

PATENT NO. : 3,937,720
DATED : February 10, 1976
INVENTOR(S) : Ravi K. Varma et al.

It is certified that error appears in the above-identified patent and that said Letters Patent are hereby corrected as shown below:

In the abstract, the second paragraph, omit "alkylthio".

Column 1, line 37, omit "alkylthio".

Column 3, line 55, omit the "1" before "11β".

Column 6, line 31, "19-" should read -- -9- --.

Column 7, renumber examples as follows:

| old | new |
|-----|-----|
| 13 | 13 |
| 14 | (omit) |
| 15 | 14 |
| 16 | (omit) |
| 17 | 15 |
| 18 | 16 |
| 19 | 17 |
| 20 | 18 |
| 21 | 19 |
| 22 | 20 |
| 23 | 21 |
| 24 | 22 |
| 25 | 23 |

Column 8, line 40, "Example 26" should read --Example 24--.

Column 9, line 32, omit "alkylthio".

Signed and Sealed this

Thirteenth Day of July 1976

[SEAL]

Attest:

RUTH C. MASON
Attesting Officer

C. MARSHALL DANN
Commissioner of Patents and Trademarks